US005529685A

United States Patent [19]
Irie et al.

[11] Patent Number: 5,529,685
[45] Date of Patent: Jun. 25, 1996

[54] DIALYSIS SYSTEM FOR RETURNING BLOOD IN THE SYSTEM AFTER THE COMPLETION OF DIALYSIS

[75] Inventors: Yasubumi Irie, Funabashi; Kenichi Kurano, Tokyo; Toshikatsu Suzuki, Tokyo; Hiroaki Ishizuka, Tokyo; Hirokazu Uehara, Tokyo; Shingo Ohwaki, Tokyo, all of Japan

[73] Assignees: Senko Medical Instrument Mfg. Co., Ltd., Tokyo; San Ai Memorial Clinic, Chiba-ken, both of Japan

[21] Appl. No.: 87,389

[22] Filed: Jul. 2, 1993

[30] Foreign Application Priority Data

Jul. 7, 1992 [JP] Japan ................................. 4-180144
Jun. 21, 1993 [JP] Japan ................................. 5-149635

[51] Int. Cl.$^6$ .......................... B01D 61/28; B01D 61/30; B01D 61/32
[52] U.S. Cl. ................... 210/134; 210/85; 210/90; 210/97; 210/98; 210/103; 210/117; 210/195.2; 210/252; 210/258; 604/4
[58] Field of Search ............... 210/85, 87, 90, 210/97, 103, 98, 134, 195.2, 252, 258, 321.6, 117; 604/4, 5, 6, 30

[56] References Cited

U.S. PATENT DOCUMENTS

| | | | |
|---|---|---|---|
| 3,946,731 | 3/1976 | Lichtenstein | 210/87 |
| 4,191,182 | 3/1980 | Popovich et al. | 210/90 |
| 4,596,549 | 6/1986 | Minami | 210/140 |
| 4,614,590 | 9/1986 | Rath et al. | 210/90 |
| 4,661,246 | 4/1987 | Ash | 210/87 |
| 4,711,715 | 12/1987 | Polaschegg | 210/103 |
| 5,120,303 | 6/1992 | Hombrouckx | 604/4 |
| 5,227,049 | 7/1993 | Chevallet et al. | 210/87 |

FOREIGN PATENT DOCUMENTS

| | | |
|---|---|---|
| 2242994 | 4/1975 | France . |
| 2513884 | 4/1983 | France . |
| 3720664A1 | 1/1987 | Germany . |
| 2110564 | 6/1983 | United Kingdom . |
| WO84/00892 | 3/1984 | WIPO . |
| WO9015631 | 12/1990 | WIPO . |

*Primary Examiner*—John Kim
*Attorney, Agent, or Firm*—Darby & Darby

[57] ABSTRACT

The dialysis apparatus in accordance with the present invention is provided with main piping connecting a blood inlet and a blood outlet, and having disposed therealong a blood pump, a dialyzer, and a venous-side chamber, in that order from the blood inlet side; and with a supplementary fluid supply mechanism, which is connected between the blood inlet and the blood pump through the medium of a branch pipe branching from the main piping; this apparatus is furthermore provided with a first clamp provided between the blood inlet and the blood pump of the main piping, a second clamp provided between the venous-side chamber and the blood outlet, and a third clamp provided on the branch pipe. In addition, by means of this dialysis apparatus, it is possible to reliably and easily return blood within the main piping of the dialysis apparatus to the body of the patient after the completion of blood dialysis.

9 Claims, 6 Drawing Sheets

DIALYSIS SYSTEM FOR RETURNING BLOOD IN THE SYSTEM AFTER THE COMPLETION OF DIALYSIS

BACKGROUND OF THE INVENTION

Field of the Invention

The present invention relates to a dialysis apparatus dialyses blood of a patient.

Figure 1:
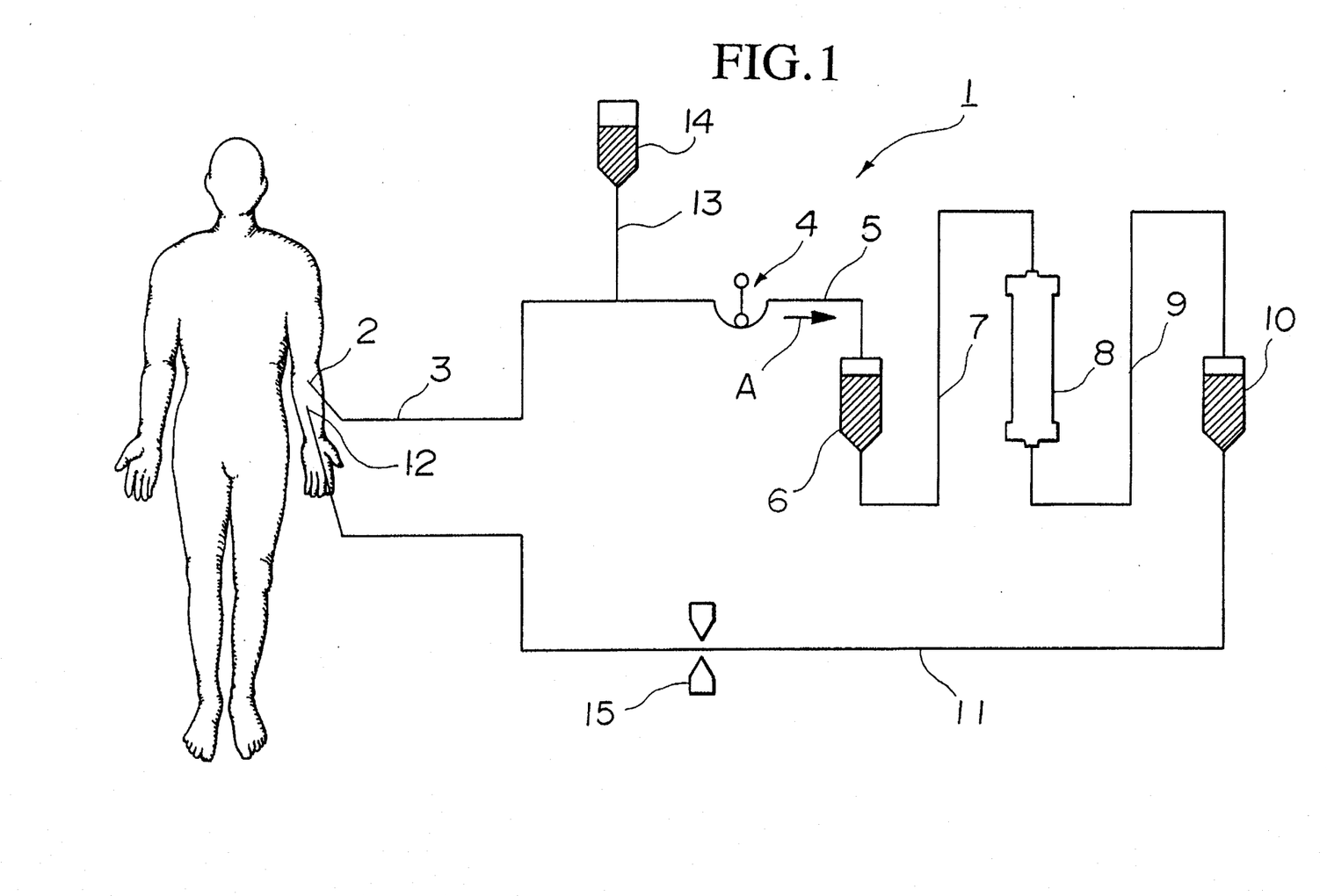
FIG. 1 is a structural outline diagram of a dialysis apparatus illustrating the composition and structure of a dialysis apparatus.

The present inventors have developed the dialysis apparatus shown in FIG. 1 as a dialysis apparatus used in blood dialysis.

As shown in FIG. 1, a blood pump 4 is connected to a first pipe 3 which is coupled with a blood inlet 2 of a patient. An arterial-side chamber 6 is connected to the blood pump 4 through the medium of a second pipe 5. A dialyzer 8 is connected to arterial chamber 6 through the medium of the third pipe 7. A venous-side chamber 10 is connected to dialyzer 8 through the medium of a fourth pipe 9. Venous-side chamber 10 is connected to blood outlet 12 through the medium of a fifth pipe 11. The first through fifth pipes 3 to 11 comprise the main piping.

Furthermore, a supplementary fluid reservoir (supplementary fluid supply mechanism) 14 is connected to the first pipe 3 through the medium of a branch pipe 13. A vein clamp 15 for opening and closing the pipe 11 is provided on the fifth pipe 11.

When dialysis of blood is conducted by means of this dialysis apparatus 1, blood pump 4 is engaged, and the blood from the body of a patient is caused to circulate within the piping of the dialysis apparatus 1 in the direction shown by arrow A in FIG. 1. When this is conducted, the blood is caused to pass through hollow capillary tubes (not depicted in the diagram) disposed within dialyzer 8, and waste products and the like which are present in the blood are removed.

That is to say, when the blood passes through the hollow capillary tubes within dialyzer 8, the waste products present in the blood are expelled into a dialysis fluid which circulates within the vessels of dialyzer 8, waste products are removed, and purified blood is returned to the body of the patient from blood outlet 12.

In this dialysis apparatus 1, after the above described blood dialysis has been completed, in order to return the blood within the piping to the body of the patient (this is termed "blood return"), the following operations are conducted.

(1) First, forceps are applied to branch pipe 13, and the flow of supplementary fluid is blocked.

(2) Next, the first pipe 3 is removed from the blood inlet 2 of the patient.

(3) Next, a separately prepared supplementary fluid reservoir is connected to this first pipe 3, and, setting the blood pump 4 to low revolutions, the blood within the piping is returned to the veins of the patient while supplying supplementary fluid from this supplementary fluid reservoir or while supplying air. At this time, observation is conducted so that gas bubbles do not enter the body of the patient, and blood pump 4 may be stopped rapidly.

However, with the above dialysis apparatus 1, the blood return operations themselves require a certain amount of training, and this operation requires a considerable amount of labor and time.

SUMMARY OF THE INVENTION

It is an object of the present invention to make possible the accurate and easy return of blood within the piping to the body of a patient after the completion of blood dialysis.

The dialysis apparatus of the present invention is provided with:

main piping, which is connected to the blood inlet and to the blood outlet and has inserted therein, in order from the blood inlet, a blood pump, a dialyzer, and a venous-side chamber;

a supplementary fluid supply mechanism, connected to the main piping between the blood inlet and the blood pump and through the medium of a branch pipe;

a first clamp, provided between the blood inlet of the main piping and the branch point at which the branch pipe is connected, and which is capable of opening and closing the main piping;

a second clamp, which is provided between the dialyzer and the blood outlet, and is capable of opening and closing the main piping; and a third clamp, which is provided on the branch pipe, and is capable of opening and closing this branch pipe.

In accordance with this dialysis apparatus, after the completion of blood dialysis, the first clamp is placed in a closed state, the second clamp is placed in a closed state, and the third clamp is placed in a open state, the blood pump is operated in the direction of normal rotation, that is to say, so that the blood is caused to move from the blood inlet in the direction of the blood outlet. Next, the first clamp is placed in an open state, the second clamp is placed in a closed state, and the third clamp is placed in a closed state, and the blood pump is operated in the direction of opposite rotation, so as to cause the blood to flow from the blood outlet in the direction of the blood inlet. Next, by repeating the above operations, the blood return of the blood amount within the piping from the blood inlet to the branch point with the branch pipe, which is previously known, is conducted. Furthermore, when the blood return on the arterial side has been completed, the first clamp is placed in a closed state, the second clamp is placed in an opened state, and the third clamp is placed in an open state, and by operating the blood pump in the direction of normal rotation, the blood return of the amount of blood within the piping from the branch point with the branch pipe to the blood outlet is conducted. That is to say, in accordance with the dialysis apparatus of the present invention, the blood within the piping can be accurately and easily returned to the body of the patient.

Furthermore, the blood return method in accordance with the present invention comprises:

an arterial blood return process, wherein, after the completion of dialysis by means of a dialysis apparatus provided with:

main piping, which is connected to a blood inlet and a blood outlet, and having disposed thereon a blood pump, an arterial-side chamber, a dialyzer, and a venous-side chamber, in that order from the blood inlet side, and a supplementary fluid supply mechanism, which is provided on a branch pipe connected between the blood inlet and the blood pump of the main piping;

a drawing process, wherein, in the state in which the section between the blood inlet and the branch point connected to the branch pipe is closed, and the section between the venous-side chamber and the blood outlet is closed, the blood pump is operated in the direction of normal rotation, and supplementary fluid is drawn into the main piping from the branch pipe, and a sending process, wherein, in the state in which the branch pipe is closed, and the section between the blood inlet and the branch point is opened, the blood pump is operated in the direction of opposite rotation, and the supplementary fluid thus drawn in is sent to the blood inlet, are repeated, and blood return is conducted by means of the replacement by the supplementary fluid in the piping between the blood inlet and the branch point; and a venous blood return process, wherein the section between the blood inlet and the branch point is closed, and the section between the branch pipe and venous-side chamber and the blood outlet is opened, the blood pump is operated in the direction of normal rotation, and supplementary fluid is drawn from the branch pipe into the piping from the branch point to the blood outlet, and by means of the replacement with this supplementary fluid in the piping, blood return is conducted.

Next, in accordance with the blood return method of the present invention, by means of the conducting of the arterial blood return process, the blood in the piping from the branch point to the blood inlet is reliably returned, and furthermore, by the means of the conducting of the venous blood return process, the blood in the piping from the branch point to the blood outlet is reliably returned.

By means of this, the return of the blood remaining within the main piping, which was conventionally an operation requiring extensive training, can be accomplished easily and reliably.

DETAILED DESCRIPTION OF THE PREFERRED EMBODIMENTS

Hereinbelow, embodiments of the dialysis apparatus and blood return method of the present invention will be explained with reference to the figures.

First, a first embodiment of the dialysis apparatus will be explained with reference to FIG. 2.

Figure 2:
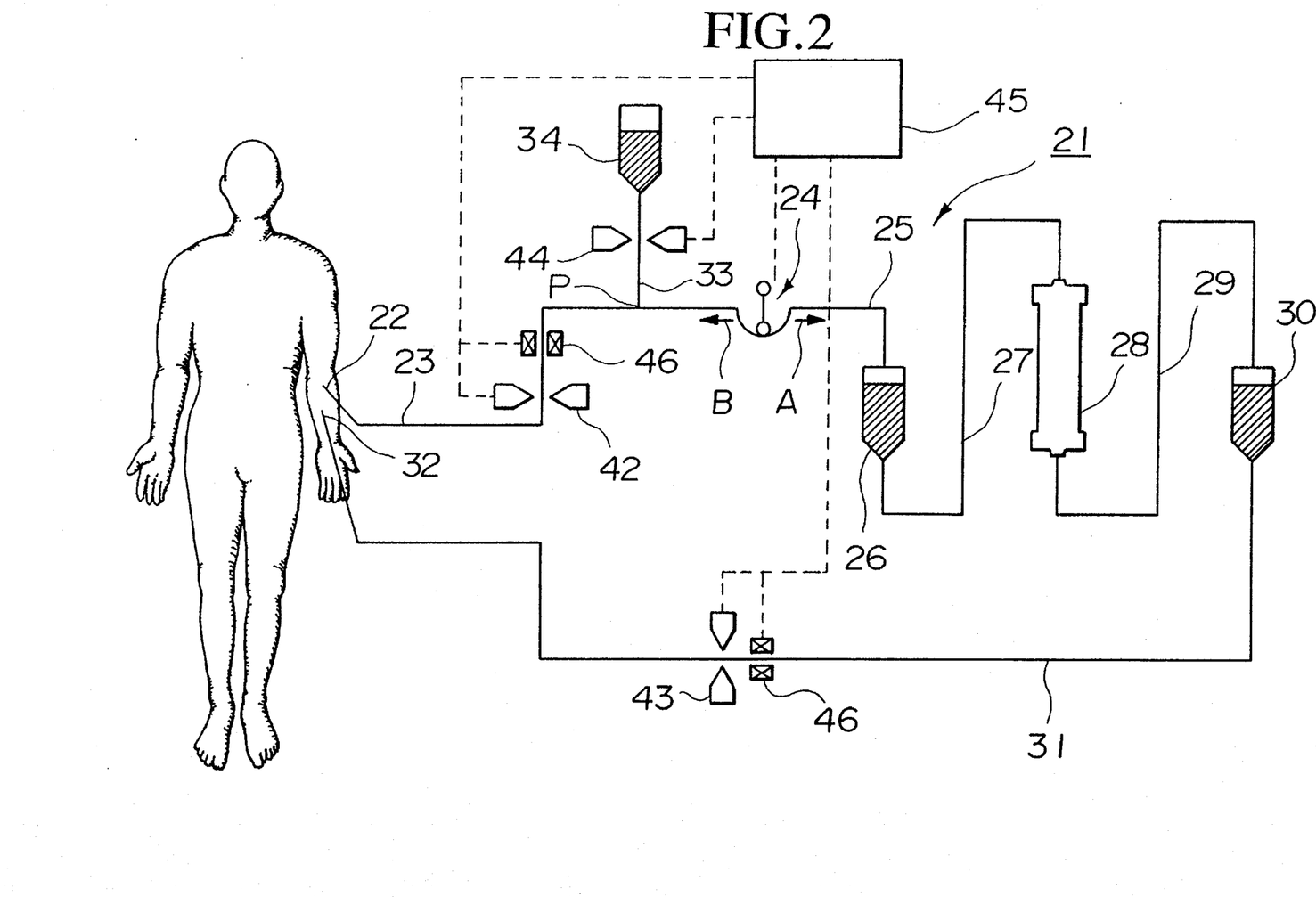
FIG. 2 is a structural outline diagram of a dialysis apparatus showing the structure and composition of a first embodiment of a dialysis apparatus.

In FIG. 2, reference numeral 21 indicates a first embodiment of the dialysis apparatus. This dialysis apparatus 21 has the following structure.

As shown in FIG. 2, a blood pump 24 is connected to a first pipe 23 which is coupled with the blood inlet 22 of a patient. An arterial-side chamber 26 is connected to this blood pump 24 through the medium of a second pipe 25. A dialyzer 28 is connected to the arterial-side chamber 26 through the medium of a third pipe 27. A venous-side chamber 30 is connected to dialyzer 28 through the medium of a fourth pipe 29. Venous-side chamber 30 is connected to a blood outlet 32 through the medium of a fifth pipe 31. First through fifth pipes 23 through 31 comprise the main piping.

Furthermore, a supplementary fluid reservoir (supplementary fluid supply mechanism) 34 is connected to the first pipe 23 through the medium of a branch pipe 33.

A first clamp 42, which opens and closes the first pipe 23, is provided on first pipe 23 at a position which is on the blood inlet 22 side of the branch point P at which the branch pipe 33 is connected, and a second clamp 43, which opens and closes the fifth pipe 31, is provided on the fifth pipe 31. A third clamp 44, which opens and closes the branch pipe 33, is provided on the branch pipe 33.

In addition, control apparatus (control mechanism) 45 is connected to blood pump 24, first clamp 42, second clamp 43, and third clamp 44; by means of this control apparatus 45, the blood flow rate and blood flow direction of blood pump 24, and the open and closed state of first clamp 42, second clamp 43, and third clamp 44, are controlled.

Furthermore, gas bubble detectors 46 and 46 are provided on first pipe 23 and fifth pipe 31 in the vicinity of blood inlet 22 and blood outlet 32, respectively, and these gas bubble detectors 46 and 46 are connected to control apparatus 45.

Arterial-side chamber 26 and venous-side chamber 30 are formed of, for example, vinyl chloride, or the like, so that they possess a certain amount of elasticity.

When the dialysis of blood is to be conducted by means of dialysis apparatus 21, blood pump 24 is engaged, and the blood from the body of the patient is caused to circulate into the piping of the dialysis apparatus 21 in the direction shown by arrow A in FIG. 2. When this is done, this blood is passed through hollow capillary tubes (not depicted in the diagram) disposed within dialyzer 28, and waste products and the like which are present in the blood are removed.

That is to say, when the blood is passed through the hollow capillary tubes of dialyzer 28, the waste products which are present in the blood are expelled to a dialysis fluid circulating within the vessels of dialyzer 28, and purified blood, from which waste products have been removed, is sent to the body of the patient from blood outlet 32.

Next, in this dialysis apparatus 21, after blood dialysis, blood return is accomplished by means of the following operations.

(1) By means of control apparatus 45, the first clamp 42 is placed in a closed state, the second clamp 43 is placed in a closed state, and the third clamp 44 is placed in an open state, pump 24 is operated in the direction of normal rotation, that is to say, operations are conducted so that blood flows from blood inlet 22 in the direction A of the blood outlet 32.

By proceeding in this manner, supplementary fluid is drawn from branch pipe 33 to the venous-side of first pipe 23, that is to say, from the branch point P to the side of the blood pump 24.

Here, by means of placing the second clamp 43 in a closed state, the flow rate of the supplementary fluid drawn to the venous-side of first pipe 23 is determined by the total capacity of the arterial-side chamber 26 and the venous-side chamber 30.

Accordingly, in this case, the rotational frequency of blood pump 24 is controlled so as to maintain the flow rate of the supplementary fluid which is thus drawn out at a level which is below the combined value of the capacities of the arterial-side chamber and the venous-side chamber 30.

(2) While maintaining the closed state of the second clamp 43, the first clamp 42 is placed in an opened state, and the third clamp 44 is placed in a closed state, blood pump 24 is operated in the direction of opposite rotation, that is to say, operations are conducted so that blood flows in the direction B of the arterial side.

At this time, the flow rate resulting from the blood pump 24 is identical to the flow rate of the supplementary fluid drawn to the venous-side in (1) above.

By proceeding in this manner, the supplementary fluid drawn to the venous-side in (1) above is sent into the first pipe 23 on the arterial-side of branch point P, and an amount of the blood within the first pipe 23 which is identical with the amount of supplementary fluid sent returns to the patient.

(3) After the operations of (2) above, the operations of (1) above are conducted, and the operations of (1) and (2) are repeatedly conducted.

By proceeding in this manner, the blood present in the piping from the branch point P of the first pipe 23 to the blood inlet 22 is all returned to the arteries of the patient, a fixed amount at a time, and the fluid in the piping from the branch point P of the first pipe 23 to the blood inlet 22 is exchanged for supplementary fluid.

Here, the amount of blood on the arterial side, that is to say, the amount of blood present in the piping from the branch point P to the blood inlet 22 is already known, so that when that amount of blood on the arterial side has been returned to the arteries of the patient, the operations of (1) and (2) are completed.

During these operations, if by any chance a gas bubble should enter the piping of the dialysis-apparatus 21, the gas bubble detector 46 detects the gas bubble in the vicinity of the blood inlet 22, and a signal is sent to control apparatus 45. Next, control apparatus 45 places the first clamp 42 in a closed state based on the signal, and thereby the entry of the gas bubble into the body of the patient can be prevented.

When the blood remaining in the piping from the branch point P of first pipe 23 to the blood inlet 22 has been returned to the patient by means of the repetition of the operations of (1) and (2) above, the blood return operation of the blood within the piping from branch point P to blood outlet 32 is conducted in the following manner.

(4) The first clamp 42 is placed in a closed state, the second clamp 43 is placed in an open state, and the third clamp 44 is placed in an open state, and blood pump 24 is operated in the direction of normal rotation, that is to say, operations are conducted so that blood flows from blood inlet 22 in the direction A of the blood outlet 32.

By proceeding in this manner, supplementary fluid is drawn into the first pipe 23 from branch point P, and the blood in the piping from branch point P to blood outlet 32 is returned to the veins of the patient.

Furthermore, in this case as well, the amount of blood on the venous side, that is to say, the amount of blood present in the piping from the branch point P to the blood outlet 32, is known in advance, so that when this amount of blood on the venous side has been returned to the veins, completion of the process is achieved.

In the case in which the supplementary fluid present in supplementary fluid reservoir 34 is smaller than the amount of blood on the venous side, a hole is opened in supplementary fluid reservoir 34 and blood return is conducted by drawing air into the piping on the venous side after drawing supplementary fluid into this piping.

In this operation, if by any chance a gas bubble should enter the piping of dialysis apparatus 21, gas bubble detector 46 detects the gas bubble in the vicinity of the blood outlet 32, and a signal is sent to control apparatus 45. Then, control apparatus 45 places the second clamp 43 in a closed state based on this signal, and thereby the entry of a gas bubble into the body of the patient can be prevented.

By means of the operations of (1), (2), and (3), above (arterial blood return process), and the operations of (4) (venous blood return process), the blood in the piping of the dialysis apparatus 21 can be reliably and easily returned to the body of the patient after the completion of blood dialysis.

Furthermore, the replenishment of body fluids by means of supplementary fluids after dialysis can also be accurately conducted by the appropriate setting of the operational conditions of control apparatus 45.

Next, a second embodiment of the dialysis apparatus will be explained with reference to FIG. 3.

In the second dialysis apparatus 51, the flow of the blood remaining within the dialyzer 28, when blood is returned to the venous-side in the first embodiment, is improved.

Figure 4:
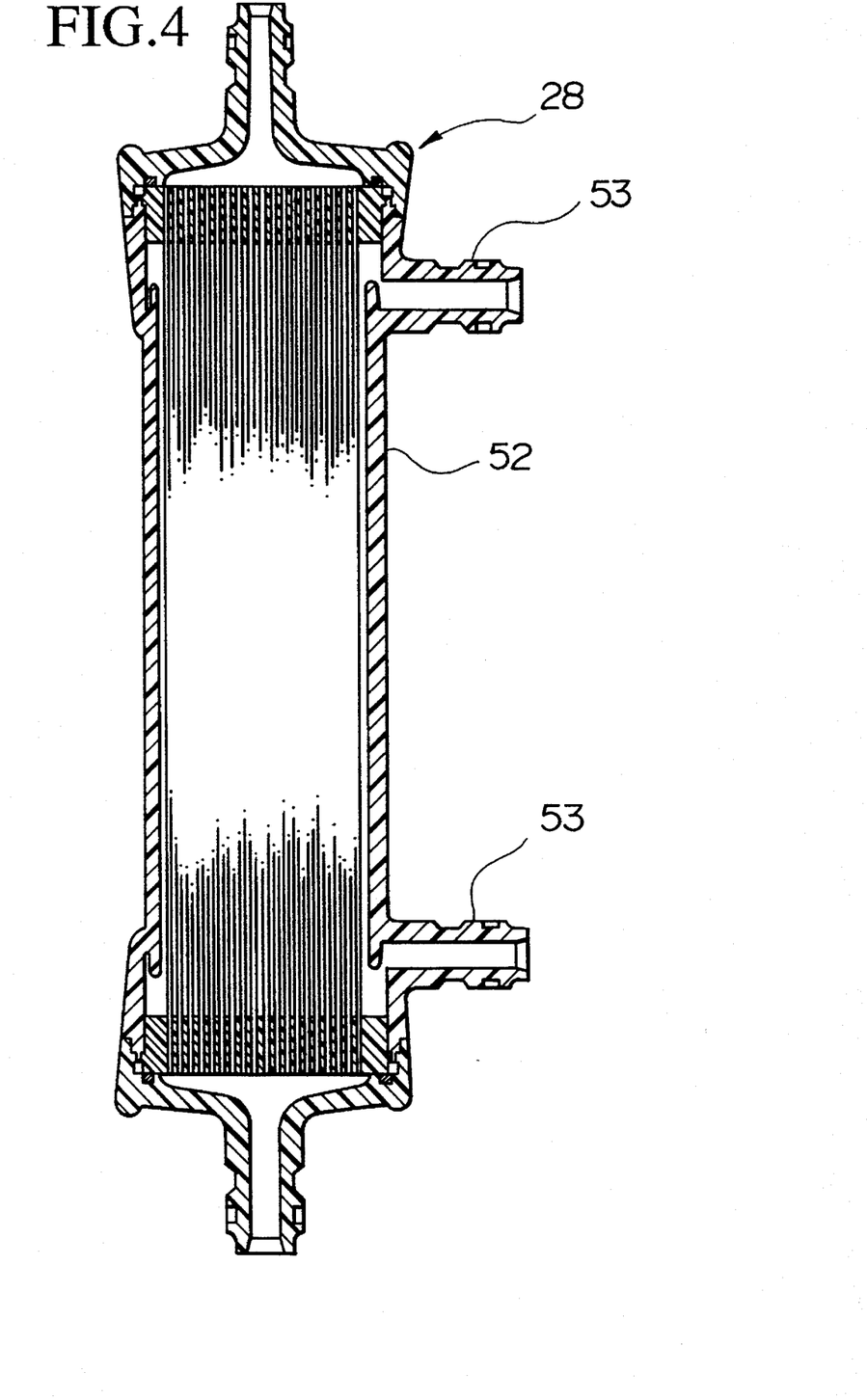
FIG. 4 is a cross sectional diagram of a dialyzer showing the structure of a dialyzer provided in the piping of the dialysis apparatus.

Here, as shown in FIG. 4, dialyzer 28 has a structure such that a plurality of hollow capillary tubes 52, 52, ... having an inner diameter of 30–1000 µm are disposed within the dialyzer and along the direction of blood flow; blood flows within these hollow capillary tubes 52, 52, ...

By means of passing blood through these hollow capillary tubes 52, 52, ..., the waste products present in the blood expelled into the dialysis fluid circulating within the vessels. Reference numeral 53 indicates a flow opening permitting the circulation of dialysis fluid within the vessels of dialyzer 28.

Accordingly, the blood remaining within the hollow capillary tubes 52, 52, ... of the dialyzer 28 cannot be caused to completely flow out merely by the passage of supplementary fluid by means of the blood pump 24.

For this reason, the second embodiment of the dialysis apparatus 51 is capable of causing the blood remaining within the dialyzer 28 to flow out, by comprising the following structure.

Figure 3:
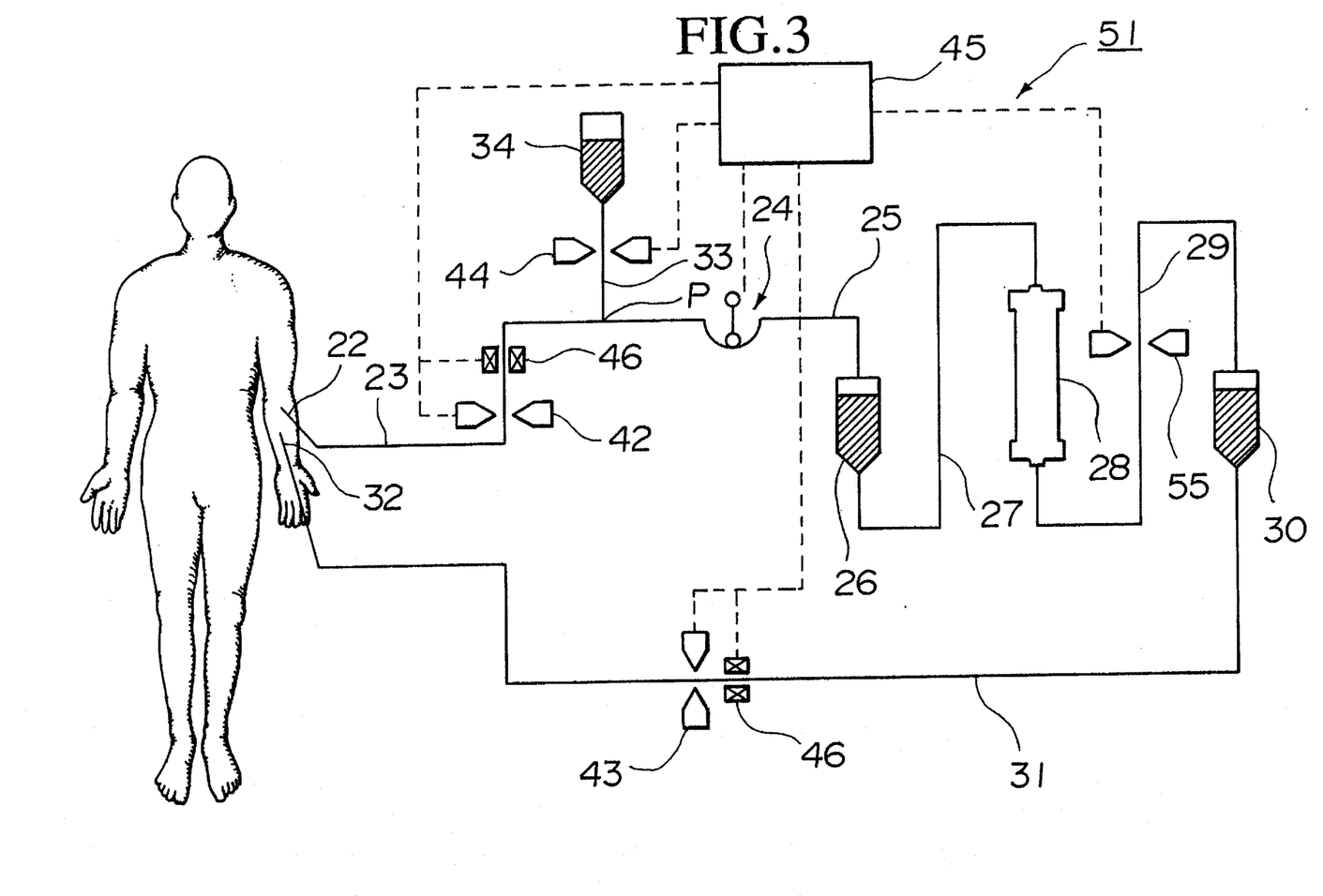
FIG. 3 is a structural outline diagram of a dialysis apparatus showing the structure and composition of a second embodiment of a dialysis apparatus.

As shown in FIG. 3, this dialysis apparatus 51 is provided with a fourth clamp 55 on fourth pipe 29, which clamp is capable of opening and closing fourth pipe 29. This fourth clamp 55 is controlled by control apparatus 45 so as to open and close during the operation (4) of the first embodiment above, in which blood is returned to the venous-side.

When this fourth clamp 55 is placed in a closed state for a predetermined period of time, as a result of the blood or the supplementary fluid sent by blood pump 24, the internal pressure of arterial-side chamber 26 and dialyzer 28 is increased to a certain extent.

Next, when this fourth claim 55 is placed in an opened state, the blood or supplementary fluid present in the piping between blood pump 24 and fourth clamp 55 is caused to powerfully flow in the direction of blood outlet 32 as a result of the internal pressure of arterial-side chamber 26 and dialyzer 28.

After this, the blood within third pipe 27 is returned, and this is replaced with supplementary fluid within third pipe 27, and after this, only supplementary fluid is caused to powerfully flow, in fixed amounts of time, into dialyzer 28. As a result of the supplementary fluid which is powerfully flowing in, the blood remaining within the hollow capillary tubes 52, 52, ... of dialyzer 28 is reliably caused to flow onward.

The predetermined time period of the closed state of the fourth clamp 55 is set so that the flow rate of the blood or supplementary fluid sent from the blood pump 24 and stored in the arterial-side chamber 26 is less than the capacity of arterial-side chamber 26.

In this way, in accordance with the second embodiment of the dialysis apparatus 51, it is possible to expel the blood remaining within dialyzer 28, the expulsion of which blood presented difficulties, by means of supplementary fluid during blood return, and it is possible to greatly increase the efficiency of the recovery operation of the blood remaining within dialyzer 28.

Figure 5:
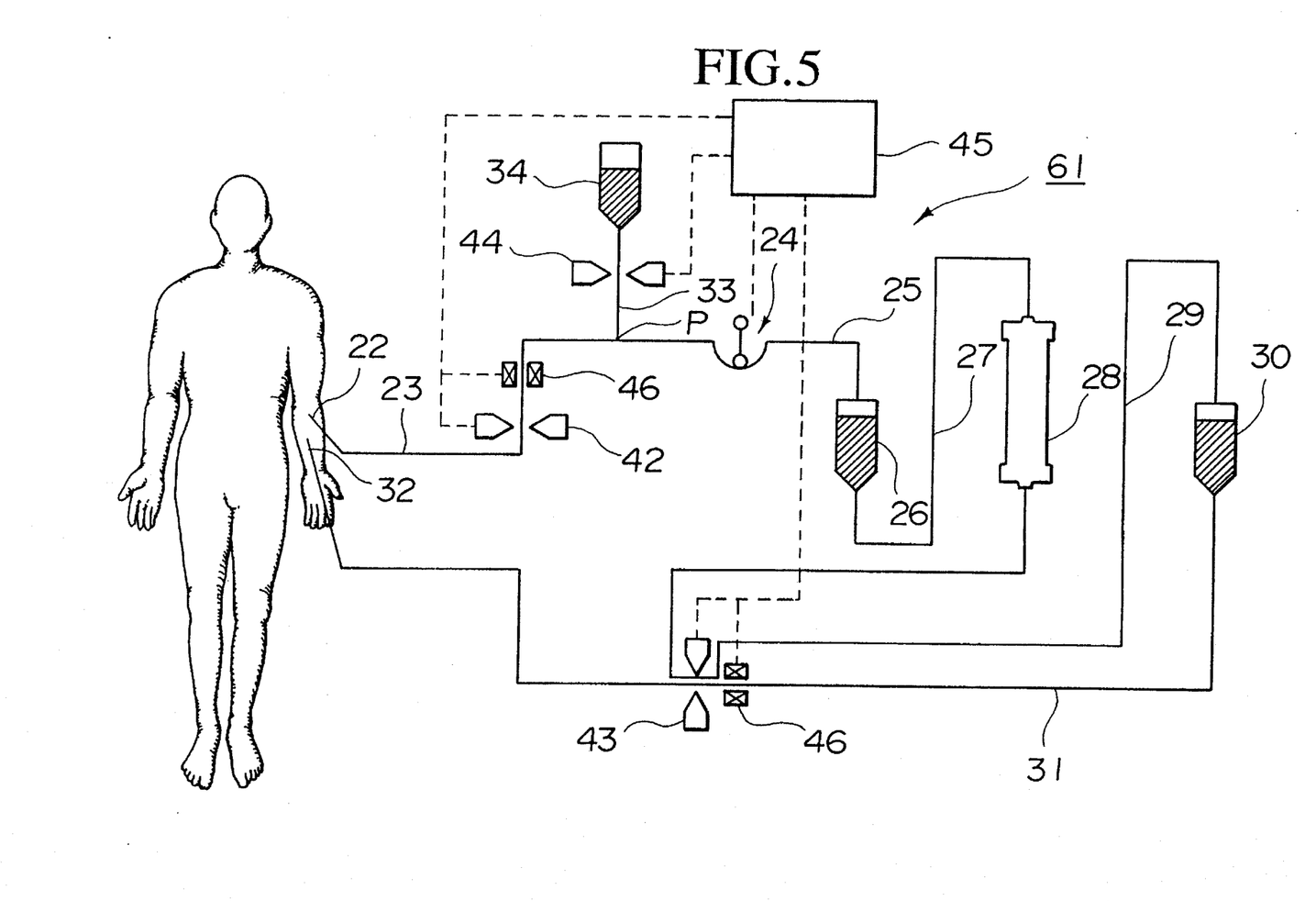
FIG. 5 is a structural outline diagram of a dialysis apparatus showing the structure and composition of a third embodiment of a dialysis apparatus.

Next, a third embodiment will be explained with reference to FIG. 5.

In this third embodiment of the dialysis apparatus 61, a portion of fourth pipe 29 is parallel to fifth pipe 31, and these parallel pipes 29 and 31 are capable of simultaneous opening and closing by means of second clamp 43.

That is to say, during the blood return operation of the blood present within the piping from branch point P to blood inlet 22, second clamp 43 is used in a manner identical to that explained in the case of the first embodiment above; during blood return operations of blood present within the piping from branch point P to blood outlet 32, this second clamp 43 is used in a manner identical to that of the fourth clamp 55 in the second embodiment.

That is to say, in this third embodiment of the dialysis apparatus 61, the functions of the fourth clamp 55 are provided by means of the second clamp 43, so that a simplification of the structure of the apparatus can be achieved.

Figure 6:
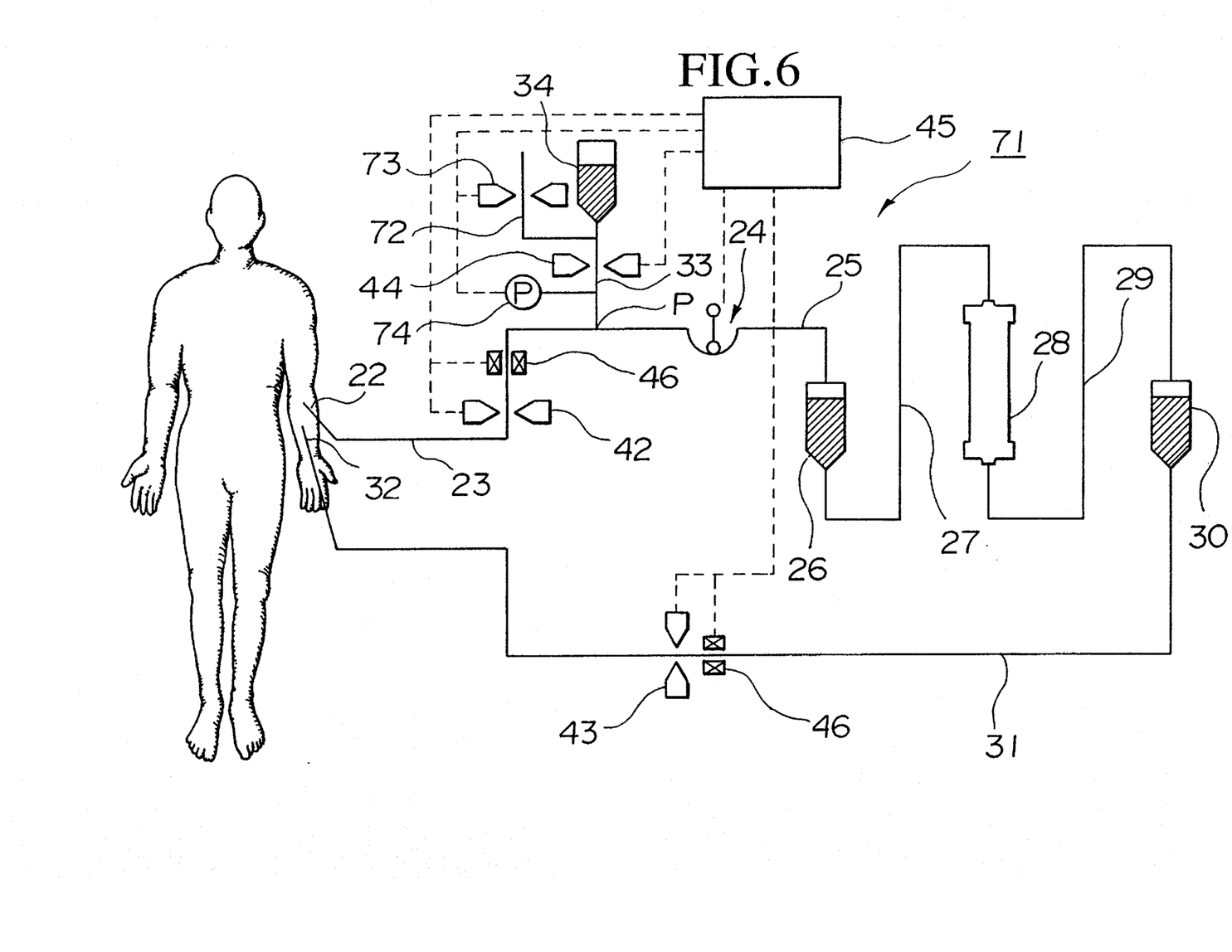
FIG. 6 is a structural outline diagram of a dialysis apparatus showing the structure and composition of a fourth embodiment of a dialysis apparatus.

Next, a fourth embodiment of the dialysis apparatus will be explained with reference to FIG. 6.

In this fourth embodiment of the dialysis apparatus 71, during the return of blood present within the piping from branch point P to blood outlet 32, after all of the supplementary fluid within supplementary fluid reservoir 34 has been used, air is automatically let into branch pipe 33.

Here, during the blood return operation, if the capacity of the supplementary fluid reservoir 34 is large, there is no need to admit air; however, the supplementary fluid reservoir 34 normally has a small capacity, so that in the case in which the supplementary fluid within supplementary fluid reservoir 34 is exhausted, it is necessary to manually open a hole in supplementary fluid reservoir 34 and allow the entry of air into branch pipe 33, and the hole-opening operation in supplementary fluid reservoir 34 requires some labor.

In this fourth embodiment of the dialysis apparatus 71, a control pipe 72 is connected to the branch pipe 33, and a fifth clamp 73, which is normally in a closed state, is provided at the end of this control pipe 72. Furthermore, a pressure sensor 74 is provided along branch pipe 33, and the detection data of this pressure sensor 74 are outputted to control apparatus 45. Based on the output data from this pressure sensor 74, control apparatus 45 conducts the opening and closing of fifth clamp 73.

That is to say, during the return of blood present within the piping from branch point P to blood outlet 32, when the supplementary fluid within supplementary fluid reservoir 34 is exhausted, and the pressure within branch pipe 33 is reduced, pressure sensor 74 detects the decline in pressure within branch pipe 33, and outputs this detection data to control apparatus 45. Control apparatus 45 then places fifth clamp 73 in a open state based on the detection data from pressure sensor 74, air enters branch pipe 33 automatically through the medium of control pipe 72, and by means of this, the blood return operation of the blood present in the piping from branch point P to blood outlet 32 can be conducted in a successful manner.

In the above embodiment, the positions at which gas bubble detectors 46 and 46, first clamp 42, and second clamp 43 are disposed is not particularly restricted.

That is to say, in the case in which gas bubble detectors 46 and 46 detect a gas bubble, piping can be closed extremely rapidly by means of first clamp 42 and second clamp 43, so that no problems will occur even if these gas bubble detectors 46 and 46 are disposed at points on the side of the patient.

What is claimed is:

1. A dialysis system for returning blood in the system after dialysis is completed comprising:

a main fluid line for establishing a fluid flow path between an inlet for receiving blood from the body of a patient and an outlet for conveying dialyzed blood to the body;

a bi-directional pump, dialysis means and venous dialyzed fluid storing means serially connected in fluid flow relationship in the recited order by said main fluid line between said main fluid line inlet and outlet, said pump being bi-directional and drawing fluid in a direction from said main fluid line inlet and pumping fluid in a direction toward said outlet when rotating in a first direction and pumping fluid toward said inlet when rotating in a second direction opposite to said first direction;

a supply of supplementary fluid having an outlet;

a branch tube connecting the outlet of said supplementary fluid supply to said main fluid line at a branch point between said main fluid line inlet and said pump to convey supplementary fluid from said supply to said main fluid line;

a first clamp cooperating with said main fluid line between said inlet and said branch point operating in the open and closed states to respectively permit and block fluid flow in said main fluid line between said inlet and said branch point;

a second clamp cooperating with said main fluid line between said venous dialyzed fluid storing means and said outlet operating in the open and closed states to respectively permit and block fluid flow in said main line between said venous dialyzed fluid storing means and said main fluid line outlet;

a third clamp cooperating with said branch tube and operating in the open and closed states to respectively permit and block fluid flow in said branch tube between said supplementary fluid supply outlet and said branch point;

control means for alternately operating said pump and said first, second and third clamps between a first condition for conducting flow of fluid including blood in said main fluid line toward said main fluid line outlet by closing said first and second clamps, opening said third clamp and operating said pump in said first direction to conduct fluid, including supplementary fluid, in said main fluid line in said first direction toward said dialysis means and said main fluid line outlet, and a second condition to open said first clamp, close said second clamp, and close said third clamp to block flow of supplementary fluid to said main flow line and operate said pump in said second direction to conduct fluid flow in said main fluid line toward said inlet.

2. A system as in claim 1 wherein after conducting the fluid return between said branch point and said inlet, said control means further operates to close said first clamp, open said second and third clamps and operate said pump in said first direction to conduct fluid flow, including supplementary fluid, from said branch point toward said outlet.

3. A system as in claim 2 further comprising a fourth clamp cooperating with said main fluid line between said dialysis means and said dialyzed fluid storing means operating open and closed states to respectively permit and block fluid flow in said main fluid line between said dialysis means and said dialyzed fluid storing means, said control means also operating to repeatedly open and close said fourth clamp during the time that fluid is being conducted from said branch point toward said outlet.

4. A system as in claim 1 further comprising a fourth clamp cooperating with said main fluid line between said dialysis means and said dialyzed fluid storing means operating open and closed states to respectively permit and block fluid flow in said main fluid line between said dialysis means and said dialyzed fluid storing means, said control means also operating to repeatedly open and close said fourth clamp during the time that fluid is being conducted from said branch point toward said outlet.

5. A dialysis system as in claim 1 further comprising an arterial side fluid storage means provided in fluid flow relationship in said main fluid line between said pump and said dialysis means.

6. A system as in claim 1 wherein said second clamp also cooperates with said main fluid line between said dialysis means and said dialyzed fluid storing means to permit and block fluid flow therebetween as said first clamp opens and closes.

7. A system as in claim 6 wherein a section of said main fluid line between said dialysis means and said dialyzed fluid storing means is in parallel with a section of said main fluid line between said dialyzed fluid storing means and said outlet and said second clamp cooperates with said parallel sections to permit and block fluid flow in said parallel sections as said second clamp opens and closes.

8. A system as in claim 1 further comprising a tubing section having one end vented to the air and the other end communicating with said branch tube, a fifth clamp cooperating with said tubing section operating in the open and closed states to respectively permit and block fluid flow in said tubing section, a pressure sensor for sensing the fluid pressure in said branch tube, said control means operating in response to a detection of a fluid pressure reduction in said branch tube during the time of fluid return between said branch point and said outlet to operate said fifth clamp to supply air through said tubing section to said branch tube.

9. A system as in claim 1 further comprising means connected to said control means for detecting the presence of gas bubbles in the fluid in said main fluid line in the vicinity of each of said inlet and outlet, said control means closing said first and second clamps upon detection of gas bubbles.

* * * * *